United States Patent [19]
Matsuyama et al.

[11] Patent Number: 5,559,030
[45] Date of Patent: Sep. 24, 1996

[54] PROCESSES FOR PRODUCTION OF OPTICALLY ACTIVE 4-HALO-3-HYDROXYBUTYRIC ACID ESTERS

[75] Inventors: Akinobu Matsuyama, Arai; Akira Tomita; Yoshinori Kobayashi, both of Joetsu, all of Japan

[73] Assignee: Daicel Chemical Industries, Ltd., Osaka, Japan

[21] Appl. No.: 180,420

[22] Filed: Jan. 12, 1994

[30] Foreign Application Priority Data

Jan. 12, 1993 [JP] Japan .................. 5-003422

[51] Int. Cl.$^6$ .................................. C12P 7/40
[52] U.S. Cl. .............. 435/280; 435/135; 435/822; 435/911
[58] Field of Search ................ 435/280, 135, 435/146

[56] References Cited

U.S. PATENT DOCUMENTS

| | | | |
|---|---|---|---|
| 4,642,290 | 2/1987 | Sih | 435/128 |
| 4,710,468 | 12/1987 | Sih | 435/135 |
| 4,933,282 | 6/1990 | Hasegawa et al. | 435/135 |
| 5,413,921 | 4/1995 | Onisai et al. | 435/135 |

FOREIGN PATENT DOCUMENTS

| | | |
|---|---|---|
| 208662 | 1/1987 | European Pat. Off. |
| 61-146191 | 7/1986 | Japan . |
| 63-123387 | 5/1988 | Japan . |
| 63-309195 | 12/1988 | Japan . |
| 01277494 | 11/1989 | Japan . |
| 2132614 | 7/1984 | United Kingdom . |

OTHER PUBLICATIONS

Shen G-J, et al., J. Chem. Soc., Chem Commun. (1990) 677–679.
Christen M. et al., J. Chem. Soc., Chem Commun. (1988) 264–266.
Patel R et al., Enzyme Microb. Technol. 14:731–738 (1992).
ATCC Catalogue of Bacteria and Bacteriophages, p. 272 (1992).
ATCC Catalogue of Yeasts, pp. 15, 90–91, 102–104 (1990).
"The Prokaryotes", eds. Balows et al, pp. 1559–1560 (1992).
"Yeasts, Characteristics and Identification", eds. Barnett et al, Entry 401 and Introduction (1986).
Fabrizio Araggozzini et al, "Biocatalytic, Enantioselective Preparations of (R)- and (S)-Ethyl 4-Chloro-3- Hydroxybutanote," A Useful Chiral Synthon, Biocatalysis 1992, vol. 5, pp. 325–332.
Bing–nan Zhou et al, "Stereochemical Control of Yeast Reductions", J. Am. Chem. Soc. 1983, 105, pp. 5925–5926.
Shimizu, S. et al., "Stereospecific Reduction of 3-Keto Acid Esters by a Novel Aldehyde Reductase of Sporobolomyces salmonicolor in a Water–Organic Solvent Two–Phasic System" Annals of the New York Academy of Sciences vol. 613:628–632 (1990).
Chemical Abstracts, vol. 117, No. 19, Abstract No. 190226h, (Nov. 1992).
Chemical Abstracts, vol. 113, No. 25, Abstract No. 229624 (Dec. 1990).
Database WPI, Section Ch, Week 8605, Derwent Publications Ltd. JP–A–60–251890 (Dec. 1985).
Database WPI, Section Ch, Week 8827, Derwent Publications Ltd., JP–A–63–123387 (May 1988).

*Primary Examiner*—David M. Naff
*Assistant Examiner*—Sandra Saucier
*Attorney, Agent, or Firm*—Cushman Darby & Cushman, L.L.P.

[57] ABSTRACT

A microorganism that is capable of acting on a 4-halo-acetoacetic acid ester shown by the general formula:

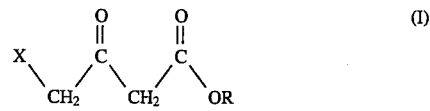

wherein X represents a halogen atom and R represents an optionally substituted alkyl group, alkenyl group, cycloalkyl group or aryl group, to produce an optically active 4-halo-3-hydroxybutyric acid ester or a preparation thereof is permitted to act on said 4-halo-acetoacetic acid ester and the product optically active 4-halo-3-hydroxybutyric acid ester is harvested. Thus, the desired optically active 4-halo-3-hydroxybutyric acid ester of high optical purity can be produced with commercial efficiency.

8 Claims, No Drawings

PROCESSES FOR PRODUCTION OF OPTICALLY ACTIVE 4-HALO-3-HYDROXYBUTYRIC ACID ESTERS

FIELD OF THE INVENTION

The present invention relates to a process for producing an optically active 4-halo-3-hydroxybutyric acid ester characterized by permitting a microorganism or a preparation thereof to act on a 4-halo-3-acetoacetic acid ester and harvesting the product optically active 4-halo-3-hydroxybutyric acid ester.

BACKGROUND OF THE INVENTION

Optically active 4-halo-3-hydroxybutyric acid esters are important intermediates for the synthesis of various medicinal compounds, optically active biologically active substances and derivatives thereof.

For the production of an optically active 4-halo-3-hydroxybutyric acid ester, there is known an asymmetric enzymatic reduction (J. Am. Chem. Soc., 105, 5925 (1988); Ann. N.Y. Acad. Sci., 613, 628 (1990); Japanese Patent Application Laid-open No. 277494/1989; etc.), as well as an asymmetric reduction with the aid of a microorganism (Japanese Patent Application Laid-open No. 146191/1986, etc.) and an asymmetric reduction with the aid of *Lactobacillus fermentum* and *Lactobacillus kelfa* (Biocatalysis, Vol. 5, pp. 325 to 332 (1992)).

The enzymatic asymmetric reduction process, however, is disadvantageous in that the process is complicated and can not be carried out with simplicity. The asymmetric reduction processes with the aid of a microorganism are also disadvantageous in that the practically sufficient efficiency of the processes and the optical purity of the product optically active compound can not be obtained and that the microorganisms usable in the reactions are extremely restricted.

Under the circumstances, the establishment of an economical and expedient process for production of an optically active 4-halo-3-hydroxybutyric acid ester of high optical purity has been demanded.

SUMMARY OF THE INVENTION

Accordingly, it is an object of the present invention to provide a process for producing an optically active 4-halo-3-hydroxybutyric acid ester of high optical purity expediently and efficiently with the aid of a microorganism.

It is another object of the invention to provide a commercially useful process for producing an optically active 4-halo-3-hydroxybutyric acid ester.

It is a further object of the invention to provide an efficient process for producing a (R)-4-halo-3-hydroxybutyric acid ester or a (S)-4-halo-3-hydroxybutyric acid ester with the aid of a microorganism.

The present inventors were interested in the utilization of a 4-halo-acetoacetic acid ester as a raw material with the aid of a microorganism for the economical and expedient production of an optically active 4-halo-3-hydroxybutyric acid ester of high optical purity and performed an extensive screening of microorganisms to find strains suited for the above purpose. As a consequence, they discovered that certain strains selected from certain genera and species of microorganisms act on a 4-halo-acetoacetic acid ester to produce either a (R)-4-halo-3-hydroxybutyric acid ester or a (S)-4-halo-3-hydroxybutyric acid ester. The present invention has been accomplished on the basis of the above finding.

Thus, present invention provides a method of producing an optically active 4-halo-3-hydroxybutyric acid ester comprising permitting a microorganism or a preparation thereof to act on a 4-halo-acetoacetic acid ester shown by the general formula:

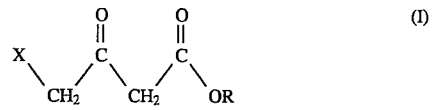

wherein X represents a halogen atom and R represents an optionally substituted alkyl group, alkenyl group, cycloalkyl group or aryl group, and harvesting the product optically active 4-halo-3-hydroxybutyric acid ester.

The microorganisms to be employed in accordance with the invention may be any strain of microorganism that is able to act on a 4-halo-acetoacetic acid ester to produce either a (S)-4-halo-3-hydroxybutyric acid ester or a (R)-4-halo-3-hydroxybutyric acid ester.

The microorganisms which is capable of producing a (S)-4-halo-3-hydroxybutyric acid ester include a strain of microorganism belonging to the genus Brevibacterium, the genus Escherichia, the genus Kluyveromyces, the genus Leucosporidium, the genus Leuconostoc, the genus Lodderomyces, the genus Oosporidium, the genus Pediococcus, the genus Pityrosporum, the genus Rhodosporidium, the genus Sporidiobolus, the genus Stephanoascus, the genus Streptococcus, the genus Saccharomycopsis, the genus Wickerhamia, the genus Zygosaccharomyces, the genus Zygoascus, *Lactobacillus buchneri*, *Lactobacillus bulgaricus*, *Lactobacillus casei*, *Lactobacillus delbrueckii*, *Lactobacillus frigidus*, *Lactobacillus hilgardii*, *Lactobacillus lactis*, *Lactobacillus malefermentans*, *Lactobacillus plantarum* and *Lactobacillus xylosus*.

The microorganisms which produce (R)-4-halo-3-hydroxybutyric acid ester include a strain of microorganism belonging to the genus Arthrobacter, the genus Leuconostoc, the genus Streptococcus, the genus Sporolactobacillus, *Lactobacillus brevis*, *Lactobacillus collinoides*, *Lactobacillus leichmannii* and *Lactobacillus viridescens*.

Such a microorganism is generally grown in a culture medium and, then, submitted to the reaction with a 4-halo-acetoacetic acid ester. A preparation of such microorganism may instead be used in the reaction with a 4-halo-acetoacetic acid ester.

DETAILED DESCRIPTION OF THE INVENTION

As the halogen atom represented by X in the 4-halo-acetoacetic acid ester shown by the formula (I) as used in the present invention, there may be mentioned chorine, bromine, iodine and so on.

Examples of the alkyl group represented by R include a straight chain or branched alkyl group having 1 to 8 carbon atoms such as methyl group, ethyl group, n-propyl group, isopropyl group, n-butyl group, i-butyl group, tert-butyl group, n-pentyl group, tert-pentyl group, hexyl group, heptyl group and octyl group.

As the alkenyl group represented by R, there may be mentioned a straight chain or branched alkenyl group having 2 to 6 carbon atoms such as vinyl group, propenyl group and 2-butenyl group.

The cycloalkyl group is exemplified as a monocycloalkyl group having 3 to 8 carbon atoms such as cyclopropyl group, cyclobutyl group, cyclopentyl group, cyclohexyl group and cycloheptyl group.

Examples of the aryl group include an aryl group having 6 to 14 carbon atoms such as phenyl group and naphthyl group.

The alkyl group, alkenyl group, cycloalkyl group or aryl group represented by R may optionally be substituted with a substituent.

As such a substituent, any one can be employed as far as the reaction is not adversely affected, thus including substituents generally employed for those groups.

Typical examples of these substituent include a halogen atom such as iodine, chlorine, fluorine and bromine, nitro group, an alkoxy group having 1 to 4 carbon atoms (for example methoxy group, ethoxy group, propoxy group, butoxy group, etc.), an aryl group having 6 to 14 carbon atoms (e.g. phenyl group, naphtyl group and the like), an alkyl group having 1 to 8 carbon atoms (for instance, methyl group, ethyl group, n-propyl group, i-propyl group, n-butyl group, i-butyl group, tert-butyl group, octyl group, etc.), a cycloalkyl group having 3 to 8 carbon atoms (e.g. cyclopentyl group, cyclohexyl group, etc.) and so on. The number of the substituents may preferably be 1 to 4.

Practically preferred examples of the group represented by R may include a straight chain or branched alkyl group having 1 to 4 carbon atoms such as methyl group, ethyl group, n-propyl group and i-propyl group, and an optionally substituted phenyl group (e.g. phenyl group, tolyl group, and the like).

The microorganisms to be employed in accordance with the invention may be any strain of microorganism that is able to act on a 4-halo-acetoacetic acid ester to produce a (S)-4-halo-3-hydroxybutyric acid ester or a (R)-4-halo-3-hydroxybutyric acid ester.

The examples of those microorganisms which are able to act on a 4-halo-acetoacetic acid ester to produce a (S)-4-halo-3-hydroxybutyric acid ester include, among others, the genus Brevibacterium, the genus Escherichia, the genus Kluyveromyces, the genus Leucosporidium, the genus Leuconostoc, the genus Lodderomyces, the genus Oosporidium, the genus Pediococcus, the genus Pityrosporum, the genus Rhodosporidium, the genus Sporidiobolus, the genus Stephanoascus, the genus Streptococcus, the genus Saccharomycopsis, the genus Wickerhamia, the genus Zygosaccharomyces, the genus Zygoascus, *Lactobacillus buchneri, Lactobacillus bulgaricus, Lactobacillus casei, Lactobacillus delbrueckii, Lactobacillus frigidus, Lactobacillus hilgardii, Lactobacillus lactis, Lactobacillus malefermentans, Lactobacillus plantarum* and *Lactobacillus xylosus*.

As typical examples of the strain of microorganism that is able to act on a 4-halo-3-acetoacetic acid ester to produce a (S)-4-halo-3-hydroxybutyric acid ester, there may be mentioned
the genus Escherichia: *Escherichia coli* IFO 3302, etc.,
the genus Brevibacterium: *Brevibacterium ammoniagenes* IFO 12072, etc.,
the genus Kluyveromyces: *Kluyveromyces lactis* IFO 1267, etc.,
the genus Leucosporidium: *Leucosporidium scottii* IFO 1924, etc.,
the genus Leuconostoc: *Leuconostoc dextranicum* IFO 3347, etc.,
the genus Lodderomyces: *Lodderomyces elongisporus* IFO 1676, etc.,
the genus Oosporidium: *Oosporidium margartiferum* IFO 1208, etc.,
the genus Pediococcus: *Pediococcus parvulus* IFO 12233, etc.,
the genus Pityrosporum: *Pityrosporum ovale* IFO 0656, etc.,
the genus Rhodosporidium: *Rhodosporidium diobovatum* IFO 1830, etc.,
the genus Sporidiobolus: *Sporidiobolus pararoseus* IFO 0376, etc.,
the genus Stephanoascus: *Stephanoascus ciferrii* IFO 1854, etc.,
the genus Streptococcus: *Streptococcus equi* NRIC 1138, etc.,
the genus Saccharomycopsis: *Saccharomycopsis capsularis* DSM 70560, etc.,
the genus Wickerhamia: *Wickerhamia fluorescens* DSM 70715, etc.,
the genus Zygosaccharomyces: *Zygosaccharomyces bailii* DSM 70492, etc.,
the genus Zygoascus: *Zygoascus hellenicus* IFO 1575, etc.,
*Lactobacillus buchneri*: *Lactobacillus buchneri* NRIC 1040, etc.,
*Lactobacillus bulgaricus*: *Lactobacillus bulgaricus* NRIC 1041, etc.,
*Lactobacillus casei*: *Lactobacillus casei* NRIC 1044, etc.,
*Lactobacillus delbrueckii*: *Lactobacillus delbrueckii* IAM 1085, etc.,
*Lactobacillus frigidus*: *Lactobacillus frigidus* NRIC 1079, etc.,
*Lactobacillus hilgardii*: *Lactobacillus hilgardii* NRIC 1060, etc.,
*Lactobacillus lactis*: *Lactobacillus lactis* DSM 20073, etc.,
*Lactobacillus malefermentans*: *Lactobacillus malefermentans* NRIC 1081, etc.,
*Lactobacillus plantarum*: *Lactobacillus plantarum* IFO 3070, etc.,
*Lactobacillus xylosus*: *Lactobacillus xylosus* NRIC 1074, etc. and the like.

The examples of those microorganisms which has capacity of acting on a 4-halo-acetoacetic acid ester to produce a (R)-4-halo-3-hydroxybutyric acid ester include those belong to the genus Arthrobacter, the genus Leuconostoc, the genus Streptococcus, the genus Sporolactobacillus, *Lactobacillus brevis, Lactobacillus collinoides, Lactobacillus leichmannii* and *Lactobacillus viridescens*.

Practical examples of the strain of microorganism that is able to act on a 4-halo-acetoacetic acid ester to produce a (R)-4-halo-3-hydroxybutyric acid ester include
the genus Arthrobacter: *Arthrobacter ureafaciens* IFO 12140, etc.,
the genus Leuconostoc: *Leuconostoc dextranicum* ATCC 17072, etc.,
the genus Streptococcus: *Streptococcus faecalis* IFO 12964, *Streptococcus faecium* NRIC 1145, Streptococcus sp. IFO 3535, etc.,
the genus Sporolactobacillus: *Sporolactobacillus inulinus* TUA 343, etc.,
*Lactobacillus brevis*: *Lactobacillus brevis* NRIC 1037, etc.,
*Lactobacillus collinoides*: *Lactobacillus collinoides* NRIC 1049, etc.,
*Lactobacillus leichmannii*: *Lactobacillus leichmannii* JCM 1557, etc.,
*Lactobacillus viridescens*: *Lactobacillus viridescens* NRIC 1073, etc. and the like.

At least one strain of microorganism among them can be employed.

For the purposes of the invention, any of wild strains, mutants and recombinant strains which can be obtained by a genetic engineering technique such as cell fusion or gene manipulation, that is able to act on a 4-halo-acetoacetic acid ester to produce an optically active 4-halo-3-hydroxybutyric acid ester can be advantageously employed.

The microorganisms identified hereinabove by IFO numbers are described in the "List of Cultures Ed. 8, Vol. 1 (1988)" published by Institute for Fermentation, Osaka (IFO), Japan and are available from the same Institute. The microorganisms designated by JCM numbers are listed in "Catalogs of Microbial Strains Ed. 4 (1989)" published by the Culture Collection of The Institute of Physical and Chemical Research, Japan and available from the same Culture Collection. The microorganisms designated by ATCC numbers are listed in "Catalogue of Bacteria Phages rDNA Vectors, Ed. 16 (1985)" and "Catalogue of Fungi/Yeast, Ed. 17 (1987)" each published by the American Type Culture Collection (ATCC) and are available from the same organization. The microorganisms designated by DSM numbers are listed in "Catalogue of Strains (1983)" of Deutsch Sammlung von Mikroorganismen (DSM) and are available from the same organization. The microorganisms designated by IAM numbers are available from Institute for Applied Microbiology of Tokyo University and the microorganisms designated by NRIC numbers and TUA numbers are available from Tokyo Agricultural University.

A microorganism, such as the above, is usually grown in a culture medium and, then, submitted to the reaction with a 4-halo-acetoacetic acid ester.

The medium which is used for growing the strain for use in the invention is not critical in composition only if the selected strain may grow and multiply therein. The medium is generally a fluid medium containing sources of carbon and nitrogen and other nutrients. Any carbon source which the strain can utilize may be employed. As the sources of carbon, there may be employed various carbohydrates such as glucose, fructose, sucrose, dextrin, starch, etc., alcohols such as sorbitol, methanol, ethanol, glycerol, etc., organic acids such as fumaric acid, citric acid, acetic acid, propionic acid, etc. and the corresponding salts, hydrocarbons such as paraffin, and various mixtures thereof. The sources of nitrogen include, among others, inorganic acid ammonium salts such as ammonium chloride, ammonium sulfate, ammonium phosphate, etc., organic acid ammonium salts such as ammonium fumarate, ammonium citrate, etc., inorganic or organic nitrogenous materials such as meat extract, yeast extract, malt extract, peptone (polypeptone), corn steep liquor, casein hydrolysate, urea, etc., and various mixtures thereof.

In the medium, there may be incorporated appropriate amounts of those nutrients which are commonly employed in the cultivation of microorganisms, such as inorganic salts, trace metal salts and vitamins. Where necessary, there may also be incorporated factors which may promote growth of the strain used and/or factors which may augment its ability to produce the object compound of the invention, such as a 4-halo-acetoacetic acid ester, as well as a buffer substance which may assist in the maintenance of the medium at a given pH.

The cultivation of the microorganism is carried out under conditions optimal for the growth of the particular strain, for example at a medium pH in the range of about 3.0 to 9.5, preferably about 4 to 8, and an incubation temperature in the range of about 20° to 45° C., preferably about 25° to 37° C. The cultivation may be aerobic or anaerobic. The cultivation time may, for example, be 5 to 120 hours, preferably about 12 to 72 hours.

The desired optically active 4-halo-3-hydroxybutyric acid ester can be produced as a 4-halo-acetoacetic acid ester is added to a dispersion of cells of the microorganism or a preparation thereof for asymmetric reduction.

The method of production of an optically active 4-halo-3-hydroxybutyric acid ester from the corresponding 4-halo-acetoacetic acid ester may, for example, be whichever of the following alternatives: (1) the method which comprises adding a 4-halo-acetoacetic acid ester to a culture broth as such, (2) the method which comprises separating the microbial cells from the culture broth, e.g. by centrifugation, resuspending the cells, either as they are or after washing with water, in a buffer solution, water or the like, and adding a 4-halo-acetoacetic acid ester to the resulting cell suspension, (3) the method which comprises using treated preparation of cells such as disrupted cells, acetone-treated cells, lyophilized cells and so on and adding the material to the resulting cell preparation, and (4) the method which comprises immobilizing these cells or preparations thereof and adding the material thereto. There are cases in which this reaction proceeds with advantage in the presence of a carbon source, such as glucose, sucrose, methanol or ethanol, which serves as an energy source.

The optimal cell concentration of the reaction system cannot be stated in general terms, for it is significantly dependent on the species or strain of microorganism employed. However, the concentration should be in the range where the efficiency of leaving the desired optically active compound intact will not be adversely affected. A typical cell concentration may for example be, on a dry cell basis, about 0.1 to 100 g/liter and preferably about 1 to 50 g/liter.

The cells may be wet viable cells or any preparation thereof, such as disrupted cells, acetone-treated cells, lyophilized cells and so on. These cells or cell preparations may be immobilized by known techniques such as the polyacrylamide gel method, sulfur-containing polysaccharide gel method (e.g. carrageenin gel method), alginic acid gel method, agar gel method and so on. The enzyme purified from such a cell preparation can also be employed. The enzyme can be obtained by using known purification processes in a suitable combination.

The corresponding 4-halo-acetoacetic acid ester can be used as it is or in the form of a solution in water or an organic solvent which will not interfere with the reaction or a dispersion prepared with a surfactant. The 4-halo-acetoacetic acid ester may be added in bolus at the beginning of the reaction or in several installments.

The reaction conditions can be selected from the ranges that will not detract from the yield of the object compound. For example, the pH of the reaction system can be selected from the range of pH about 3 to 10 and preferably pH about 5 to 9. The reaction temperature can be selected from the range of, for example, 10° to 60° C. and preferably from 20° to 40° C. The reaction can be conducted with stirring or under stationary conditions for about 1 to 120 hours. The concentration of a 4-halo-acetoacetic acid ester as the substrate is not particularly critical and is preferably about 0.1 to 20 weight % and more preferably about 0.2 to 10 weight %.

The optically active 4-halo-3-hydroxybutyric acid ester produced by the reaction can be harvested by the separation and purification procedures generally known. For example, the optically active 4-halo-3-hydroxybutyric acid ester can be easily obtained by subjecting the reaction mixture, directly or after separation of the cells, to the conventional purification procedure such as extraction with an organic solvent, distillation and column chromatography. The optical purity of optically active 4-halo-3-hydroxybutyric acid ester can be measured by high performance liquid chromatography (HPLC) using an optical resolution column.

Thus, according to the method of the present invention using a microorganism or preparation thereof, an optically active 4-halo-3-hydroxybutyric acid ester of high optical purity can be produced expediently and efficiently, therefore the method is commercially useful.

The following examples are intended to illustrate the invention in further detail and should by no means be construed as delimiting the scope of the invention.

EXAMPLES

In the examples, the quantitative determination of ethyl 4-chloro-3-hydroxybutyrate in reaction mixture was carried out by subjecting ethyl 4-chloro-3-hydroxybutyrate obtained by the reaction to gas chromatography using a column (column: Thermon 3000, Chromosorb W; length: 2 m; the column temperature: 140° C.). The optical purity determination thereof was carried out by subjecting the optically active 4-halo-3-hydroxybutyric acid ester to removing the solvent off, then directly to high performance liquid chromatography using an optical resolution column (column: Chiralpack AS, Daicel Chemical Industries, Ltd.; moving phase: n-hexane/isopropyl alcohol/ethanol/cyclohexanol= 92/2.5/1.25/0.25; wavelength: 220 nm; flow rate: 1 ml/min.). Under the above operating conditions, the retention time of ethyl 4-chloro-3-hydroxybutyrate was 13.8 minutes for (S) and 15.1 minutes for (R).

EXAMPLE 1

A test tube of 21 mm in diameter was charged with 5 ml of the following growth medium and, after sterilization, was inoculated with one of the microbial stains shown in Tables 1 to 4. The inoculated tube was incubated under shaking at 30° C. for 48 hours. Subsequently cells were isolated by centrifuging to obtain viable cells.

| (A) Growth medium for a yeast | |
|---|---|
| Glucose | 2.0 weight % |
| Yeast extract | 0.3 weight % |
| Malt extract | 0.3 weight % |
| Polypeptone | 0.5 weight % |
| pH | 6.0 |

| (B) Growth medium for a bacterium | |
|---|---|
| Glucose | 2.0 weight % |
| Yeast extract | 0.3 weight % |
| Meat extract | 0.3 weight % |
| Polypeptone | 0.5 weight % |
| Ammonium sulfate | 0.2 weight % |
| Potassium primary phosphate | 0.1 weight % |
| Magnesium sulfate | 0.05 weight % |
| pH | 7.0 |

| (C) Growth medium for a lactic acid bacterium | |
|---|---|
| Glucose | 2.0 weight % |
| Yeast extract | 1.0 weight % |
| Polypeptone | 1.0 weight % |
| Sodium acetate | 1.0 weight % |
| Magnesium sulfate | 0.02 weight % |
| Manganese sulfate | 1 ppm |
| Ferrous sulfate | 1 ppm |
| Sodium chloride | 1 ppm |
| Calcium carbonate | 1 weight % |
| pH | 6.8 |

Then, a test tube of 21 mm in diameter was charged with 2.5 ml of 0.1M potassium phosphate buffer (pH 6.5) containing 125 mg of glucose and said viable cells were suspended therein. Afterwards, 25 μl of ethyl 4-chloroacetoacetate was added to the suspension and the reaction was conducted on a reciprocating shaker at 30° C. for 48 hours.

After completion of the reaction, 1 ml of the reaction suspension was extracted with 2 ml of ethyl acetate. The ethyl acetate extract was subjected to gas chromatography to determine the amount of the product ethyl 4-chloro-3-hydroxybutyrate.

Then, after the solvent was removed with use of a rotary evaporator to give a syrup. The syrup was dissolved in n-hexane and the absolute configuration and optical purity of the optically active ethyl 4-chloro-3-hydroxybutyrate were determined using high performance liquid chromatography. The results are set forth in Tables 1 to 4.

TABLE 1

| Name of Microorganism | Product amount of ethyl 4-chloro-3-hydroxybutyrate (mg/ml) | Absolute configuration | Optical purity (% e.e.) |
|---|---|---|---|
| Brevibacterium ammoniagenes IFO 12072 | 3.0 | S | 96 |
| Escherichia coli IFO 3302 | 0.9 | S | 82 |
| Kluyveromyces lactis IFO 1267 | 7.7 | S | 99 |
| Lactobacillus buchneri NRIC 1040 | 10.0 | S | 46 |
| Lactobacillus bulgaricus NRIC 1041 | 2.7 | S | 90 |
| Lactobacillus casei NRIC 1044 | 3.5 | S | 99 |
| Lactobacillus delbrueckii IAM 1085 | 4.0 | S | 67 |
| Lactobacillus frigidus NRIC 1079 | 5.1 | S | 72 |
| Lactobacillus hilgardii NRIC 1060 | 7.8 | S | 92 |

TABLE 2

| Name of Microorganism | Product amount of ethyl 4-chloro-3-hydroxybutyrate (mg/ml) | Absolute configuration | Optical purity (% e.e.) |
|---|---|---|---|
| Lactobacillus lactis DSM 20073 | 4.4 | S | 63 |
| Lactobacillus malefermentans NRIC 1081 | 6.9 | S | 99 |
| Lactobacillus plantarum IFO 3070 | 10.0 | S | 99 |
| Lactobacillus xylosus NRIC 1074 | 7.3 | S | 95 |
| Leuconostoc dextranicum IFO 3347 | 8.9 | S | 57 |
| Leucosporidium scottii IFO 1924 | 7.1 | S | 37 |
| Lodderomyces elongisporus IFO 1676 | 4.6 | S | 70 |
| Oosporidium margaritiferum IFO 1208 | 3.8 | S | 58 |

TABLE 2-continued

| Name of Microorganism | Product amount of ethyl 4-chloro-3-hydroxybutyrate (mg/ml) | Absolute configuration | Optical purity (% e.e.) |
| --- | --- | --- | --- |
| *Pediococcus parvulus* IFO 12233 | 6.2 | S | 83 |

TABLE 3

| Name of Microorganism | Product amount of ethyl 4-chloro-3-hydroxybutyrate (mg/ml) | Absolute configuration | Optical purity (% e.e.) |
| --- | --- | --- | --- |
| *Pityrosporum ovale* IFO 0656 | 2.7 | S | 72 |
| *Rhodosporidium diobovatum* IFO 1830 | 7.1 | S | 39 |
| *Saccharomycopsis capsularis* DSM 70560 | 3.5 | S | 99 |
| *Sporidiobolus pararoseus* IFO 0376 | 3.4 | S | 48 |
| *Stephanoascus ciferrii* IFO 1854 | 2.7 | S | 99 |
| *Streptococcus equi* NRIC 1138 | 3.6 | S | 42 |
| *Wickerhamia fluorescens* DSM 70715 | 4.5 | S | 40 |
| *Zygosaccharomyces bailii* DSM 70492 | 3.5 | S | 66 |
| *Zygoascus hellenicus* IFO 1575 | 3.5 | S | 67 |

TABLE 4

| Name of Microorganism | Product amount of ethyl 4-chloro-3-hydroxybutyrate (mg/ml) | Absolute configuration | Optical purity (% e.e.) |
| --- | --- | --- | --- |
| *Arthrobacter ureafaciens* IFO 12140 | 2.1 | R | 70 |
| *Lactobacillus brevis* NRIC 1037 | 2.1 | R | 86 |
| *Lactobacillus collinoides* NRIC 1049 | 4.0 | R | 73 |
| *Lactobacillus leichmannii* JCM 1557 | 3.2 | R | 89 |
| *Leuconostoc dextranicum* ATCC 17072 | 2.8 | R | 94 |
| *Lactobacillus viridescens* NRIC 1073 | 7.3 | R | 73 |
| *Sporolactobacillus inulinus* TUA 343 | 1.5 | R | 49 |
| *Streptococcus faecalis* IFO 12964 | 1.3 | R | 86 |
| *Streptococcus faecium* NRIC 1145 | 1.6 | R | 82 |
| *Streptococcus sp.* IFO 3535 | 2.1 | R | 92 |

What is claimed is:

1. A process for producing (S)-4-halo-3-hydroxybutyric acid ester which comprises treating a 4-halo-acetoacetic acid ester represented by the general formula (I):

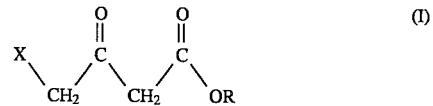

wherein X represents a halogen atom and R represents an alkyl group having 1 to 4 carbon atoms with at least one member selected from the group consisting of a microorganism, a culture broth thereof and a preparation from the microorganism capable of acting on said 4-halo-acetoacetic acid ester represented by the general formula (I), wherein said preparation is selected from the group consisting of a crude extract, disrupted cells, acetone-treated cells, lyophilized cells, immobilized cells, immobilized disrupted cells, immobilized acetone-treated cells and immobilized lyophilized cells, and said microorganism is selected from the group consisting of *Kluyveromyces lactis, Leucosporidium scottii, Leuconostoc dextranicum* IFO 3349, *Lodderomyces elongisporus, Oosporidium margaritiferum, Pediococcus parvulus, Pityrosporum ovale, Rhodosporidium diobovatum, Sporidiobolus pararoseus, Stephanoascus ciferrii, Streptococcus equi, Saccharomycopsis capsularis, Wickerhamia fluorescens, Zygosaccharomyces bailii, Zygoascus hellenicus, Lactobacillus buchneri, Lactobacillus bulgaricus, Lactobacillus casei, Lactobacillus delbrueckii, Lactobacillus frigidus, Lactobacillus hilgardii, Lactobacillus lactis, Lactobacillus malefermentans, Lactobacillus plantarum* and *Lactobacillus xylosus* to produce (S)-4-halo-3-hydroxybutyric acid ester; and recovering said (S)-4-halo-3-hydroxybutyric acid ester.

2. A process for producing (R)-4-halo-3-hydroxybutyric acid ester which comprises treating a 4-halo-acetoacetic acid ester represented by the general formula (I):

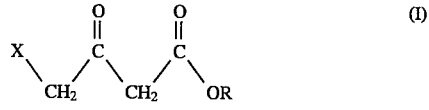

wherein X represents a halogen atom and R represents an alkyl group having 1 to 4 carbon atoms with at least one member selected from the group consisting of a microorganism, a culture broth thereof and a preparation from the microorganism capable of acting on said 4-halo-acetoacetic acid ester represented by the general formula (I), wherein said preparation is selected from the group consisting of a crude extract, disrupted cells, acetone-treated cells, lyophilized cells, immobilized cells, immobilized disrupted cells, immobilized acetone-treated cells and immobilized lyophilized cells, and said microorganism is selected from the group consisting of *Arthrobacter ureafaciens, Leuconostoc dextranicum* ATCC 17072, *Streptococcus faecalis, Streptococcus faecium,* Streptococcus sp. IFO 3535, *Sporolactobacillus inulinus, Lactobacillus brevis, Lactobacillus collinoides, Lactobacillus leichmannii* and *Lactobacillus viridescens* to produce (R)-4-halo-3-hydroxybutyric acid ester; and recovering said (R)-4-halo-3-hydroxybutyric acid ester.

3. The process according to claim 1 or 2, which comprises growing the microorganism in a fluid medium and adding said 4-halo-acetoacetic acid ester represented by the general formula (I) to a dispersion of the microorganism or the preparation from the microorganism.

4. The process according to claim 1 or 2, which comprises permitting the microorganism or the preparation from the microorganism to act on said 4-halo-acetoacetic acid ester represented by the general formula (I) at a pH of 3 to 10 and at a temperature of 10° to 60° C.

5. The process according to claim 1 or 2, wherein the process is conducted in a reaction medium and the concentration of said 4-halo-acetoacetic acid ester represented by the general formula (I) is 0.1 to 20 weight % relative to the reaction medium.

6. The process according to claim 1 or 2, which comprises permitting the microorganism or the preparation from the microorganism to act on said 4-halo-acetoacetic acid ester represented by the general formula (I) in the presence of a carbon source.

7. A process for producing (S) 4-halo-3-hydroxybutyric acid ester which comprises treating a 4-halo-acetoacetic acid ester represented by the general formula (I):

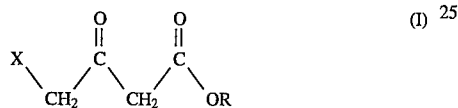

wherein X represents a halogen atom and R represents an alkyl group having 1 to 4 carbon atoms with at least one member selected from the group consisting of a microorganism, a culture broth thereof and preparation from the microorganism capable of acting on said 4-halo-acetoacetic acid ester represented by the general formula (I), wherein said preparation is selected from the group consisting of a crude extract, disrupted cells, acetone-treated cells, lyophilized cells, immobilized cells, immobilized disrupted cells, immobilized acetone-treated cells and immobilized lyophilized cells, and said microorganism is selected from the group consisting of *Lactobacillus buchneri, Lactobacillus bulgaricus, Lactobacillus casei, Lactobacillus delbrueckii, Lactobacillus frigidus, Lactobacillus hilgardii, Lactobacillus lactis, Lactobacillus malefermentans, Lactobacillus plantarum* and *Lactobacillus xylosus* to produce (S)-4-halo-3-hydroxybutyric acid ester; and recovering said (S)-4-halo-3-hydroxybutyric acid ester.

8. A process for producing (R)-4-halo-3-hydroxybutyric acid ester which comprises treating a 4-halo-acetoacetic acid ester represented by the general formula (I):

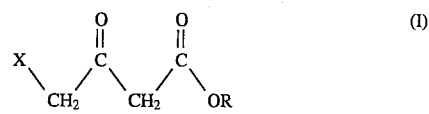

wherein X represents a halogen atom and R represents an alkyl group having 1 to 4 carbon atoms with at least one member selected from the group consisting of microorganism, a culture broth thereof and a preparation from the microorganism capable of acting on said 4-halo-acetoacetic acid ester represented by the general formula (I), wherein said preparation is selected from the group consisting of a crude extract, disrupted cells, acetone-treated cells, lyophilized cells, immobilized cells, immobilized disrupted cells, immobilized acetone-treated cells and immobilized lyophilized cells, and said microorganism is selected from the group consisting of *Arthrobacter ureafaciens, Leuconostoc dextranicum, Streptococcus faecalis, Streptococcus feacium,* Streptococcus sp. IFO 3535 and *Sporolactobacillus inulinus* to produce (R)-4-halo-3-hydroxybutyric acid ester; and recovering said (R)-4-halo-3-hydroxybutyric acid ester.

\* \* \* \* \*